US009173989B2

(12) United States Patent
Larm et al.

(10) Patent No.: US 9,173,989 B2
(45) Date of Patent: Nov. 3, 2015

(54) METHOD FOR EXTRACORPOREAL REMOVAL OF A PATHOGENIC MICROBE, AN INFLAMMATORY CELL OR AN INFLAMMATORY PROTEIN FROM BLOOD

(75) Inventors: Olle Larm, Bromma (SE); Tomas Bergström, Göteborg (SE)

(73) Assignee: EXTHERA MEDICAL CORPORATION, Berkeley, CA (US)

( * ) Notice: Subject to any disclaimer, the term of this patent is extended or adjusted under 35 U.S.C. 154(b) by 1164 days.

(21) Appl. No.: 12/086,126

(22) PCT Filed: Dec. 13, 2006

(86) PCT No.: PCT/SE2006/001421
§ 371 (c)(1),
(2), (4) Date: Sep. 10, 2008

(87) PCT Pub. No.: WO2007/069983
PCT Pub. Date: Jun. 21, 2007

(65) Prior Publication Data
US 2009/0136586 A1 May 28, 2009

(30) Foreign Application Priority Data
Dec. 13, 2005 (SE) ...................................... 0502750

(51) Int. Cl.
A61K 35/14 (2015.01)
A01N 1/02 (2006.01)
A61M 1/36 (2006.01)
A61K 31/70 (2006.01)

(52) U.S. Cl.
CPC .............. *A61M 1/3679* (2013.01); *A61K 31/70* (2013.01)

(58) Field of Classification Search
CPC ............................ A61M 1/3679; A61K 31/70
USPC .............................................. 435/2; 424/529
See application file for complete search history.

(56) References Cited

U.S. PATENT DOCUMENTS

| | | | |
|---|---|---|---|
| 4,103,685 A | 8/1978 | Lupien et al. | |
| 4,613,665 A | 9/1986 | Larm | |
| 4,820,302 A | 4/1989 | Woodroof | |
| 5,211,850 A | 5/1993 | Shettigar et al. | |
| 5,437,861 A | 8/1995 | Okarma et al. | |
| 5,447,859 A | 9/1995 | Prussak | |
| 6,159,377 A | 12/2000 | Davankov et al. | |
| 6,197,568 B1 * | 3/2001 | Marks et al. | 435/239 |
| 6,461,665 B1 | 10/2002 | Scholander | |
| 6,559,290 B1 | 5/2003 | Nakatani et al. | |
| 6,653,457 B1 | 11/2003 | Larm et al. | |
| 8,663,148 B2 | 3/2014 | Larm et al. | |
| 8,758,286 B2 | 6/2014 | Ward et al. | |
| 2002/0058032 A1 | 5/2002 | Hirai et al. | |
| 2002/0068183 A1 | 6/2002 | Huang et al. | |
| 2002/0197249 A1 | 12/2002 | Brady et al. | |
| 2002/0197252 A1 | 12/2002 | Brady et al. | |
| 2003/0021780 A1 | 1/2003 | Smith et al. | |
| 2003/0044769 A1 | 3/2003 | Ogino et al. | |
| 2004/0202783 A1 | 10/2004 | Baumann et al. | |
| 2006/0093999 A1 | 5/2006 | Hei | |
| 2007/0218514 A1 | 9/2007 | Smith et al. | |
| 2008/0021365 A1 | 1/2008 | Kobayashi et al. | |
| 2008/0138434 A1 | 6/2008 | Brady et al. | |
| 2009/0105194 A1 | 4/2009 | Flengsrud et al. | |
| 2010/0069816 A1 | 3/2010 | Brady et al. | |
| 2010/0098666 A1 | 4/2010 | Wright | |
| 2010/0216226 A1 | 8/2010 | Hyde et al. | |
| 2010/0217173 A1 | 8/2010 | Hyde et al. | |
| 2010/0249689 A1 | 9/2010 | Larm et al. | |
| 2010/0276359 A1 | 11/2010 | Ippommatsu et al. | |
| 2011/0184377 A1 | 7/2011 | Ward et al. | |
| 2011/0224645 A1 | 9/2011 | Winqvist et al. | |
| 2012/0040429 A1 | 2/2012 | Federspiel et al. | |

(Continued)

FOREIGN PATENT DOCUMENTS

DE 4217917 A1 12/1993
EP 0533946 A1 3/1993

(Continued)

OTHER PUBLICATIONS

Montelius et al, Biomaterials 1994, 15, 805-814.*
Dubreuil et al., Effect of Heparin Binding on Helicobacter Pylori Resistance to Serum, Journal of Medical Microbiology, vol. 53, pp. 9-12, 2004.
English translation of the Chinese Office Action dated Mar. 23, 2011 for Application No. 200680052757.9.
English translation of the Russian Office Action dated Sep. 1, 2010 for Application No. 2008128416.

(Continued)

*Primary Examiner* — Tekchand Saidha
*Assistant Examiner* — Md. Younus Meah
(74) *Attorney, Agent, or Firm* — Kilpatrick Townsend & Stockton LLP

(57) ABSTRACT

The present invention relates to a method for extracorporeal removal of a pathogenic microbe, an inflammatory cell or an inflammatory protein from mammalian blood/use of a device comprising a carbohydrate immobilized on a solid substrate, said carbohydrate having a binding affinity for a pathogenic microbe, an inflammatory cell or an inflammatory protein, for extracorporeal removal of said pathogenic microbe, inflammatory cell or inflammatory protein from mammalian blood/ use of a carbohydrate having a binding affinity for a pathogenic microbe, an inflammatory cell or an inflammatory protein, wherein said carbohydrate is immobilized on a solid substrate, in the preparation of a device for treatment of a condition caused or aggravated by said pathogenic microbe, inflammatory cell or inflammatory protein/and a method for treatment of a mammalian subject suffering from a condition caused or aggravated by a pathogenic microbe, an inflammatory cell or an inflammatory protein.

11 Claims, No Drawings

(56) References Cited

U.S. PATENT DOCUMENTS

| | | |
|---|---|---|
| 2012/0305482 A1 | 12/2012 | McCrea et al. |
| 2014/0012097 A1 | 1/2014 | McCrea et al. |
| 2014/0131276 A1 | 5/2014 | Larm et al. |
| 2014/0231357 A1 | 8/2014 | Ward et al. |

FOREIGN PATENT DOCUMENTS

| | | |
|---|---|---|
| EP | 1044696 A2 | 10/2000 |
| JP | 4-89500 A | 3/1992 |
| JP | 6040926 A | 2/1994 |
| JP | 96-510166 A | 10/1996 |
| JP | 2000086688 A | 3/2000 |
| JP | 2000-217575 A | 8/2000 |
| JP | 2000-515543 A | 11/2000 |
| JP | 2002-505101 A | 2/2002 |
| JP | 2005-514127 A | 5/2005 |
| WO | 94/26399 A1 | 11/1994 |
| WO | WO9505400 * | 2/1995 |
| WO | 97/35660 A1 | 10/1997 |
| WO | WO-98/05341 A1 | 2/1998 |
| WO | WO-99/45104 A3 | 11/1999 |
| WO | 03/057356 A2 | 7/2003 |
| WO | 2007/058592 A1 | 5/2007 |
| WO | 2007/069983 A1 | 6/2007 |
| WO | 2007/146162 A2 | 12/2007 |
| WO | 2008/157570 A2 | 12/2008 |
| WO | 2010/029317 A2 | 3/2010 |
| WO | 2011/068897 A1 | 6/2011 |
| WO | 2011/100354 A1 | 8/2011 |
| WO | 2012/112724 A1 | 8/2012 |
| WO | 2013/188073 A1 | 12/2013 |
| WO | 2014/209782 A1 | 12/2014 |

OTHER PUBLICATIONS

Kim et al., "Role of the Heparin in Regulating a Transcapillary Exchange in Far North Conditions", Bullentin of the Siberian Branch of the Russian Academy of Medical Sciences, No. 2, vol. 108, 2003.
Lopatkin et al., "Efferent Methods in Medicine, M., Medicine", pp. 266, 272-273, 276-279, 1989.
New Zealand Examination Report issued Apr. 14, 2010, in corresponding New Zealand Application No. 568754.
Examination Report issued on Jul. 20, 2011 in corresponding New Zealand Application No. 568754.
English translation of Office Action issued Jul. 10, 2012, in corresponding Japanese Patent Application No. 2008-545539.
Bjorklund, et al., Abstract of Synthesis of silica-based heparin-affinity adsorbents, Journal of Chromatograph A. 728(1-2) pp. 149-169, 1996.
Nadkarni, et al., Abstract of "Directional immobilization of heparin onto beaded supports," Anal Biochem, Oct. 1994; 222(1); 59-67.
Sasaki, et al., Abstract of "Improved method for the immobilization of heparin," J. Chromatogr, Jul. 29, 1987; 400; 123-32.
Zhou et al, Abstract of Heparin-Agarose aqueous ethanol suspension, Journal of Molecular Biolog, 271(3) 12, 1997.
Supplementary European Search Report issued in corresponding European Application No. EP 06835845 issued on Mar. 26, 2013.
English translastion of Decision of Refusal issued on Mar. 19, 2013, in corresponding Japanese Application No. 2008-545539.
JP Interrogation for Appl. No. 2008-545539 dated Mar. 18, 2014.
Bindslev et al., "Treatment of acute respiratory failure by extracorporeal carbon dioxide elimination performed with a surface heparinized artificial lung," Anesthesiology, 67(1):117-120, 1987.
Chen et al., "Microbial subversion of heparin sulfate proteoglycans," Mol. Cells, 26:415-426, 2008.
Dixon et al., "Anthrax," New England Journal of Medicine, 341(11):815-826, 1999.
Haase et al., "The effect of three different miniaturized blood purification devices on plasma cytokine concentration in an ex vivo model of endotoxinemia," Int. J. Artif. Organs, 31(8):722-729, 2008.
International Preliminary Report on Patentability, Aug. 21, 2013, PCT Application No. PCT/US2012/025316; 8 pages.
International Search Report; PCT/US2012/025316 mailed May 23, 2012.
International Search Report; PCT/US2010/058596 mailed Mar. 29, 2011.
International Search Report; PCT/US2011/024229 mailed May 30, 2011.
International Search Report; PCT/SE2006/001421 mailed Mar. 30, 2007.
International Search Report; PCT/US2013/042377 mailed Sep. 9, 2013.
International Search Report; PCT/US2014/043358 mailed Dec. 1, 2014.
Keuren et al., "Thrombogenecity of polysaccharide-coated surfaces," Biomaterials, 24:1917-1924, 2003.
Larm et al., "A new non-thrombogenic surface prepared by selective covalent binding of heparin via a modified reducing terminal residue," Biomater Med Devices Artif Organs, 11(2&3):161-173, 1983.
Mandal, "Sialic acid binding lectins," Experientia, 46:433-439, 1990.
Mariano et al, "Tailoring high-cut-off membranes and feasible application in sepsis-associated acute renal failure: in vitro studies," Nephrol Dial Transplant, 20:1116-1126, 2005.
Ofek et al., "Mannose binding and epithelial cell adherence of *Escherichia coli*," Infection and Immunity, 22(1):247-254, 1978.
Popova et al., "Acceleration of epithelial cell syndecan-1 shedding by anthrax hemolytic virulence factors," BMC Microbiolgy, 6:8, pp. 1-16, 2006.
Riesenfeld et al., "Quantitative analysis of N-sulfated, N-acetylated, and unsubstituted glucosamine amino groups in heparin and related polysaccharides," Anal Biochem, 188:383-389, 1990.
Sagnella et al., "Chitosan based surfactant polymers designed to improve blood compatibility on biomaterials," Colloids and Surfaces B: Biointerfaces, 42:147-155, 2005.
Sanchez, J. et al., "Control of contact activation on end-point immobilized heparin: The role of antithrombin and the specific antithrombin-binding sequence," J. Bio. Mat. Res., 29:665-661, 1995.
Schefold et al., "A novel selective extracorporeal intervention in sepsis: immunoadsorption of endotoxin, interleukin 6, and complement-activating product 5A," Shock, 28(4):418-425, 2007.
Sharon, "Bacterial lectins, cell-cell recognition and infectious disease," FEBS letters, 217(2):145-157, 1987.
Swartz, "Recognition and management of anthrax—an update," New England Journal of Medicine, 345(22):1621-1626, 2001.
Thomas et al., "Common oligosaccharide moieties inhibit the adherence of typical and atypical respiratory pathogens," Journal of Microbiology, 53:833-840, 2004.
Weber et al., "Development of specific adsorbents for human tumor necrosis factor-$\alpha$: influence of antibody immobilization on performance and biocompatibility," Biomacromolecules, 6:1864-1870, 2005.
Wendel et al., "Coating-techniques to improve the hemocompatibility of artificial devices used for extracorporeal circulation," European Journal of Cardio-thoracic Surgery, 16:342-350, 1999.
Fujita, Masanori et al., Artificial Organs, 2002, vol. 26, No. 12, pp. 1020-1025.
Hirmo, Siiri et al., "Sialyglycoconjugate- and proteoglycan-binding microbial lectins", Institute of Medical Microbiology, University of Lund, (Online). Retrieved Oct. 19, 1997, (Retrieved on Mar. 16, 2004). Retrieved from the Internet: <URL :http//vmw.plab.ku:dk/tcbh/Lectins12/Hirmo/paper.htm . . . >.
Wier, D. M., FEMS Microbiology Immunology, 1989, vol. 47, pp. 331-340.

* cited by examiner

METHOD FOR EXTRACORPOREAL REMOVAL OF A PATHOGENIC MICROBE, AN INFLAMMATORY CELL OR AN INFLAMMATORY PROTEIN FROM BLOOD

FIELD OF THE INVENTION

The present invention relates to a method for extracorporeal removal of a pathogenic microbe, an inflammatory cell or an inflammatory protein from mammalian blood; use of a device comprising a carbohydrate immobilized on a solid substrate, said carbohydrate having a binding affinity for a pathogenic microbe, an inflammatory cell or an inflammatory protein, for extracorporeal removal of said pathogenic microbe, inflammatory cell or inflammatory protein from mammalian blood; use of a carbohydrate having a binding affinity for a pathogenic microbe, an inflammatory cell or an inflammatory protein, wherein said carbohydrate is immobilized on a solid substrate, in the preparation of a device for treatment of a condition caused or aggravated by said pathogenic microbe, inflammatory cell or inflammatory protein; and a method for treatment of a mammalian subject suffering from a condition caused or aggravated by a pathogenic microbe, an inflammatory cell or an inflammatory protein.

BACKGROUND

Biology

During a long evolution, many pathogenic micro-organisms have learned to exploit eukaryotic cell surface glycoconjugates, i.e. glycolipids, glycoproteins and proteoglycans, as receptor molecules for cell attachment to facilitate tissue colonization and invasion processes. In brief, specific proteins called adhesins of the surface of bacteria, viruses, fungi and parasites interact with carbohydrate chains of glycoconjugates which enable microbes to colonize mucosal surfaces and tissue lesions.

The role of sialic acid in binding of pathogens to host cells has been reported over many years. Only recently proteoglycans with their carbohydrate chains (glycosaminoglycans) were shown to bind many different pathogens. By removing terminal carbohydrate moieties of these various glycoconjugates with sialidase and other exoglycosidases or with glycosaminoglycan (GAG) degrading enzymes on the cells in monolayers, these structures were proven to be receptor molecules for various sialoadhesins and heparan sulfate binding proteins (HeBPs).

These mechanisms are summarized in a review article by Siiri Hirmo, Meeme Utt and Torkel Wadström, Biology, Biochemistry, Clinical Biochemistry, Volume 12, including Proceedings from the 17th International Lectin Meeting in Würzburg, 1997, edited by Edilbert van Driessche, Sonia Beeckmans and Thorkild C. Bøg-Hansen, published by TEXTOP, Lemchesvej 11, DK-2900 Hellerup, Denmark, ISBN number 87-984583-0-2.

During microbial infections, inflammatory mediators are released and activated. These so-called "pro-inflammatory cytokines" include tumor necrosis factor alpha and beta (TNF-α and TNF-β), interleukin-1 (IL-1), and interleukin-6 (IL-6). These cytokines are part of the inflammatory response of sepsis. Multiple organ failure induced by sepsis is currently the leading cause of death in intensive care units.

In connection with microbial infections and cardiovascular surgery, for instance cardiopulmonary bypass, inflammatory responses are elicited and have a multitude of biological consequences, ranging from subclinical organ dysfunction to severe multiorgan failure. Cytokines are thought to be important mediators in this response.

The cytokines mentioned above have a capacity to bind selectively to a range of glycosaminoglycans, or GAGs, including heparan sulfate in tissues and on the surface of both endothelial cells and leucocytes.

Receptors

Heparan sulfate is a glycosaminoglycan that is present on the surface of almost all mammalian cells. It is built up by alternating D-glucosamine and uronic acid residues (L-iduronic and D-glucuronic). Heparan sulfates are highly charged (sulfated) heterogeneous polysaccharides and represent the carbohydrate portion of many glycoconjugates (syndecan, perlecan, glypican) on the cell surface.

Many microbes utilize heparan sulfates on the surface of the mammalian cell as receptors. This mechanism is general and valid for almost all bacteria, virus and parasites. Some microorganisms utilize more than one glycoconjugate receptor. Examples of other receptors that are used together with heparan sulfate are specific chondroitin sulfates and sialic acid containing glycoproteins.

Heparan sulfate/chondroitin sulfate binding microbes are exemplified by viruses like herpes simplex virus type 1 (HSV-1), causative agent of orolabial herpes; herpes simplex virus type 2 (HSV-2), causative agent of genital herpes; cytomegalovirus (CMV), the major complicating agent in immunosuppressed patients; dengue virus, which causes recurrent fevers; and human immunodeficiency virus (HIV); and by bacteria like *Helicobacter pylori, Streptococcus sanguis, Streptococcus mutans, Staphylococcus aureus, Escherichia coli, Pseudomonas aeruginosa*, and *Mycobacterium tuberculosis*; and parasites like *Plasmodium falciparum* (which causes malaria), and *Trypanosoma cruzi* (which causes trypanosomiasis).

Further, cytokines, like TNF-β, also utilize heparan sulfate on cell surfaces for binding and activation.

Heparin as a Receptor

Heparin is a polysaccharide, which is isolated from mammalian tissue. Since its discovery in 1916 by the American scientist McLean, heparin has been recognized for its blood anticoagulant properties and heparin has, for more than 50 years, been used clinically as a blood anticoagulant and antithrombotic agent.

Whereas heparan sulfates are ubiquitous components of all tissue-organized animal life forms, heparin has a very particular distribution in mammalian tissue. Heparin is, in contrast to the heparan sulfates, present only in the basophilic granules of mast cells. However, today, in addition to its established place in prevention and therapy of thromboembolic disorders, heparin has demonstrated a broad spectrum of different activities independent of anticoagulation.

A large number of proteins in blood bind, with high affinity, to heparin and/or heparan sulfate. Examples are antithrombin (AT), fibronectin, vitronectin, growth factors (e.g. the fibroblast growth factors, the insulin like growth factors etc). Human serum albumin (HSA) also binds, but with a lower affinity. On the other hand, HSA is present in large amounts in blood.

To utilize these properties of heparin for hindering infections, introducing heparin fragments and/or sialic containing fragments into the vascular system has been contemplated. Thereby, it was thought, these fragments would bind to the lectins on the microbes, block them and thus hinder them from binding to the receptors on the mammalian cell surface. This concept has been tried by many scientists but with limited success, in most cases due to bleeding complications when large amounts of heparin are introduced into the vascular system.

U.S. Pat. No. 6,197,568 dicloses methods for isolation and detection of flaviviruses and other hemorrhagic fever viruses, such as dengue virus, based on the sulfated polyanion-dependent interaction of flaviviruses and hemorrhagic fever viruses.

Extracorporeal devices are used in a variety of clinical situations including kidney dialysis, cardiopulmonary bypass and plasmapheresis.

"Extracorporeal therapies" means procedures in which desired products like oxygen, blood-anticoagulants, anesthetics etc can be added to body fluids. Conversely, undesired products like toxins etc can be removed from body fluids outside the body. Examples are haemodialysis and haemofiltration which represent technologies whereby blood is rinsed from waste products.

SUMMARY OF THE INVENTION

An object of the present invention is to provide a method for treatment of a mammal suffering from diseases or conditions caused or aggravated by different pathogenic microbes, inflammatory cells or inflammatory proteins by removal of said pathogenic microbes, inflammatory cells or inflammatory proteins from the blood of said mammal.

Another object of the present invention is to provide a method for extracorporeal removal of pathogenic microbes, inflammatory cells or inflammatory proteins from mammalian blood.

The above mentioned objects, as well as further objects of the invention, which should be apparent to a person skilled in the art after having studied the description below, are accomplished by the different aspects of the present invention as described herein.

A first aspect of the present invention provides a method for extracorporeal removal of a pathogenic microbe, an inflammatory cell or an inflammatory protein from mammalian blood, comprising the steps:
  a) providing a sample of mammalian blood,
  b) bringing said sample into contact with a carbohydrate immobilized on a solid substrate, said carbohydrate having a binding affinity for a pathogenic microbe, inflammatory cell or inflammatory protein, under conditions allowing binding of any pathogenic microbes, inflammatory cells and inflammatory proteins in said blood sample to the carbohydrate,
  c) separating the sample from the solid substrate, such that said pathogenic microbe, inflammatory cell or inflammatory protein is at least partially retained on the solid substrate, and
  d) recovering said sample containing a reduced amount of said pathogenic microbe, inflammatory cell or inflammatory protein.

The prior-art concept of introducing heparin fragments and/or sialic containing fragments into the vascular system of patients has shown limited success, in most cases due to bleeding complications when large amounts of heparin are introduced into the vascular system. The method according to the invention circumvents these problems by the carbohydrates being immobilized on a solid surface, as is inter alia described in Preparatory example 6.

Use of immobilized carbohydrates as defined by the method according to the invention also provides a further unexpected advantage. The inventors have found that the carbohydrate has to be immobilized onto a solid surface to have the capacity that is necessary for binding a significant amount of the compounds that are to be removed. This unexpected property is described in Comparative example 1 and Example 1 for HSV-1, showing that in solution, less than 3% of the virus binds to an excess of heparin (Comparative example 1) while more than 94% of the virus binds to immobilized heparin (Example 1).

The method of the present invention enables safe and efficient treatment of patients suffering from sepsis or septic shock by removing pathogens causative of the condition from the patient's blood stream. The method of the present invention allows removal of many different pathogenic microbes, inflammatory cells and inflammatory proteins. Examples of pathogenic microbes commonly associated with sepsis that may be removed using the method of the invention include staphylococci, such as *Staphylococcus aureus*, streptococci and *E. coli*.

As both heparin and heparan sulfates bind to a large number of components, as exemplified in the background section, it was expected that a heparin surface would be covered with many of these proteins, when brought into contact with blood, thus preventing the microbes from attaching. The present inventors have surprisingly found that highly efficient purification of serum and whole blood from mammals, including humans, can be achieved using a method and a device according to the present invention. It is disclosed herein that a column of moderate size managed to almost completely remove considerable amounts of viruses from blood serum and whole blood. See e.g. Examples 2, 3 and 4.

In an embodiment, said pathogenic microbe is selected from the group consisting of bacteria, viruses and parasites.

In an embodiment, said pathogenic microbe is a virus. In a more specific embodiment, said virus is selected from the group consisting of herpes simplex virus type 1, herpes simplex virus type 2, Influenza A virus, cytomegalovirus and human immunodeficiency virus. In another more specific embodiment, said virus is selected from the group consisting of herpes simplex virus type 1 or herpes simplex virus type 2.

In another embodiment, said pathogenic microbe is a bacterium. In a more specific embodiment, said bacterium is selected from the group consisting of *Helicobacter pylori, Streptococcus sanguis, Streptococcus mutans, Staphylococcus aureus, Escherichia coli, Pseudomonas aureginosa* and *Mycobacterium tuberculosis*. In a preferred embodiment, said pathogenic microbe is *Helicobacter pylori* or *Staphylococcus aureus*.

In yet another embodiment, said pathogenic microbe is a parasite. In a more specific embodiment, said parasite is selected from the group consisting of *Plasmodium falciparum* and *Trypanosoma cruzi*.

In a further embodiment, said inflammatory cell is selected from the group consisting of inflammatory lymphocytes and inflammatory macrophages.

In yet a further embodiment, said inflammatory protein is a pro-inflammatory cytokine. In a more specific embodiment, said pro-inflammatory cytokine is selected from the group consisting of tumor necrosis factor alpha (TNF-α), tumor necrosis factor beta (TNF-β), interleukin-1 (IL-1), and interleukin-6 (IL-6).

In an embodiment, said mammalian blood is human blood.

In an embodiment of the inventive method, said carbohydrate is selected from the group consisting of heparin, heparan sulfate, chondroitin sulfate, carbohydrates comprising sialic acid and carbohydrates comprising neuramic acid. In a more specific embodiment, said carbohydrate is heparin.

In yet another embodiment, said solid substrate comprises microparticles or hollow fibres. In certain embodiments of the invention, the material of said solid substrate is selected from the group consisting of glass, cellulose, cellulose acetate, chitin, chitosan, crosslinked dextran, crosslinked agarose, polypropylene, polyethylene, polysulfone, polyacrylonitrile, silicone, Teflon and polyurethanes.

In a further embodiment, said carbohydrate is covalently linked to said solid substrate. In a more specific embodiment, said carbohydrate is linked to said solid substrate by covalent end-point attachment. Covalent attachment of a carbohydrate to a solid substrate provides better control of parameters such as surface density and orientation of the immobilized molecules as compared to non-covalent attachment. These parameters have been shown by the inventors to be important in order to provide optimal pathogen binding to the immobilized carbohydrate molecules. The surface concentration of the carbohydrate on the solid substrate should preferably be in the range of 1-10 $\mu g/cm^2$. Covalent end-point attachment means that the carbohydrate is covalently attached to the solid substrate via the terminal residue of the carbohydrate molecule. A second aspect of the present invention provides use of a device comprising a carbohydrate immobilized on a solid substrate, said carbohydrate having a binding affinity for a pathogenic microbe, an inflammatory cell or an inflammatory protein, for extracorporeal removal of a pathogenic microbe, inflammatory cell or inflammatory protein from mammalian blood.

Embodiments of a use according to the second aspect of the invention correspond to those specified above for the method according to the first aspect of the present invention regarding the pathogenic microbe, inflammatory cell, inflammatory protein, mammalian blood, carbohydrate, solid substrate and immobilization.

A third aspect of the invention provides use of a carbohydrate having a binding affinity for a pathogenic microbe, an inflammatory cell or an inflammatory protein, wherein said carbohydrate is immobilized on a solid substrate, in the preparation of a device for treatment of a condition caused or aggravated by a pathogenic microbe, inflammatory cell or inflammatory protein.

Embodiments of a use according to the third aspect of the invention correspond to those specified above for the method according to the first aspect of the present invention regarding the pathogenic microbe, inflammatory cell, inflammatory protein, mammalian blood, carbohydrate, solid substrate and immobilization.

A device as referred to in the use and method according to the invention may comprise a conventional device for extracorporeal treatment of blood and serum from patients, e.g. suffering from renal failure.

Local blood flow patterns in blood contacting medical devices for extracorporeal circulation are known to influence clot formation via shear activation and aggregation of platelets in stagnant zones. Consequently, a device as used in the second, third and fourth aspects of the invention should be designed in a fashion that does not create these problems.

A device as used in some embodiments of the invention may for example have the following properties:
- A blood flow in the range of 1-500 ml/min, preferably 5-250 ml/min.
- Low flow resistance.
- Large surface area of substrate having carbohydrates immobilized thereto, e.g. about 0.1-1 $m^2$.
- Stable coating (no leakage of carbohydrate to the blood in contact therewith).
- Proper haemodynamic properties in the device (no stagnant zones).
- Optimal biocompatibility.

A non-limiting example of such a device, which can be used in a use or a method according to the present invention, is a pediatric haemoflow dialyzer such as the Prisma M10 haemofilter/dialyzer from Gambro AB, Sweden. Other models or types of devices for extracorporeal treatment of blood or serum may also be used.

A fourth aspect of the present invention provides a method for treatment of a mammalian subject suffering from a condition caused or aggravated by a pathogenic microbe, an inflammatory cell or an inflammatory protein, comprising the steps:
a) extracting blood from the subject,
b) bringing the extracted blood into contact with a device comprising a carbohydrate immobilized on a solid substrate, said carbohydrate having a binding affinity for a pathogenic microbe, an inflammatory cell or an inflammatory protein, under conditions allowing binding of a pathogenic microbe, an inflammatory cell or an inflammatory protein to the carbohydrate, and
c) reintroducing the blood, containing a reduced amount of said pathogenic microbe, inflammatory cell or inflammatory protein, into the blood-stream of the subject.

In an embodiment of the treatment method according to the present invention, the extraction and reintroduction of blood is performed in a continuous loop, which loop comprises a part of the bloodstream of the subject.

Embodiments of a method for treatment according to the fourth aspect of the invention correspond to those specified above for the method according to the first aspect of the present invention regarding the pathogenic microbe, inflammatory cell, inflammatory protein, mammalian blood, carbohydrate, solid substrate and immobilization.

As used herein, the term "pathogenic microbe" means a microbe, which can cause disease in a living organism when introduced into said organism. Examples of "pathogenic microbes" include bacteria, viruses and parasites.

As used herein, the term "inflammatory cell" means a cell, which is involved in inflammatory response in a mammal. Examples of "inflammatory cells" include inflammatory lymphocytes and inflammatory macrophages.

As used herein, the term "inflammatory protein" means a protein, such as a cytokine, released for instance in connection with microbial infection or immunization.

As used herein, the term "cytokine" means a protein, released for instance in connection with microbial infection or immunization, selected from the group consisting of interleukins, interferons, chemokines and tumour necrosis factors.

EXAMPLES

Preparatory Example 1

Amination of Sephadex G 25

Sodium metaperiodate ($NaIO_4$, 6.0 g) was dissolved in water (994 ml) and added to Sephadex G 25 (Pharmacia Biotech, Uppsala, Sweden) (50 g) in 1 l water. The mixture was kept in the dark under shaking for 24 h. After filtration and washing with water 5×1 l and finally 0.1 M phosphate buffer, pH 7.0, the resulting product was suspended in phosphate buffer, pH 7.0 (350 ml) and a solution of polyethylenimine (100 ml Lupasol (BASF, Germany), 5% in water) was added. The gel was stabilized by addition of an aqueous solution of $NaBH_3CN$, sodium cyanoborohydride (0.5 g in 100 ml, phosphate buffer, 0.1 M, pH 7.0). The gel was filtered and washed as described above and finally washed with acetate buffer (500 ml, 0.1 M, pH 4.0), yielding aminated Sephadex G 25 (85 g).

Preparatory Example 2

Covalent End-Point Attachment of Heparin onto a Chromatographic Gel

Aminated Sephadex G 25 (85 g) obtained as described in Preparatory example 1 was suspended in acetate buffer (800 ml, 0.1 M, pH 4.0) and 4.0 g nitrous acid degraded heparin (heparin from Pharmacia, Sweden) was added. After shaking for 0.5 h, NaBH$_3$CN (0.4 g) was added. The reaction mixture was shaken for 24 h and then processed as above, yielding heparinized Sephadex G 25 (80 g).

The gel contains 2% heparin (w/w, sulfur analysis). The Sephadex G 25 beads have an average diameter of 50-150 μm. A rough calculation reveals that 1 cm$^3$ contains 10$^6$ beads which gives a bead surface area of 0.03 m$^2$/cm$^3$. Further, if heparin is attached only to the surface of the beads, a heparinized Sephadex G 25 with 2% heparin w/w has about 0.003 μg heparin/cm$^2$.

Preparatory Example 3

Covalent Attachment of Heparin onto Aminated Glass Wool

A glass wool material is heparinized using the general procedure described below.

Glass wool is thoroughly cleaned with acid (HCl), rinsed with absolute ethanol, and dried in an oven at 100° C. for 4 hours.

Reactive amino functions are introduced on the glass wool surface by treatment with an aqueous solution of polyamine, polyethylenimine (PEI) or chitosan. For some purposes, the polyamines may be stabilized on the surface by crosslinking with bifunctional reagents, such as crotonaldehyde or glutaraldehyde.

The coating is further stabilized by ionic cross linking with a sulfated polysaccharide (dextran sulfate or heparin). If necessary, these steps are repeated and a sandwich structure is built up. Careful rinsing (water, suitable buffers) should be performed between each step. After a last addition of PEI or chitosan, end-point attachment (EPA) to the aminated surface of native heparin is done by reductive amination, utilizing the aldehyde function in the reducing terminal residue in native heparin. The coupling is performed in aqueous solution, by reductive amination (cyanoborohydride, CNBH$_3^-$) essentially as described in Preparatory example 2.

Surface analysis as described in Preparatory example 2 reveals that approximately 10 mg/cm$^2$ of heparin is coupled to the glass surface.

Preparatory Example 4

Covalent Attachment of Heparin onto Aminated Polymeric Surfaces

A polymeric surface was heparinized using the general procedure described below.

The polymeric surface is etched with a oxidizing agent (potassium permanganate, ammoniumperoxidisulfate) in order to introduce hydrophilic characteristics together with some reactive functional groups (—SO$_3$H, —OH, —C=O, —C=C—). The surface can also be etched with plasma or corona.

Reactive amino functions are introduced by treatment with a polyamine, polyethylenimine (PEI) or chitosan. For some purposes the polyamines may be stabilized on the surface by cross linking with bifunctional reagents, such as crotonaldehyde or glutaraldehyde.

The coating is further stabilized by ionic cross linking with a sulfated polysaccharide (dextran sulfate or heparin). If necessary these steps are repeated and a sandwich structure is built up. Careful rinsing (water, suitable buffers) should be performed between each step. After a last addition of PEI or chitosan, end-point attachment (EPA) to the aminated surface of native heparin is done by reductive amination, utilizing the aldehyde function in the reducing terminal residue in native heparin. A more reactive aldehyde function in the reducing terminal residue can be achieved by partial, nitrous degradation of heparin. This shortens the reaction time, but the immobilized heparin will have a lower molecular weight. The coupling is performed in aqueous solution, by reductive amination (cyanoborohydride, CNBH$_3^-$) essentially as described in Preparatory example 2.

1-10 μg/cm$^2$ of heparin can be coupled to all hydrophilic surfaces like glass, cellulose, chitin etc, and more or less all hydrophobic polymers like polyvinyl chloride, polyethylene, polycarbonate, polystyrene, PTFE etc.

Preparatory Example 5

Covalent Single- or Multipoint Attachment of Heparin onto Polymeric Surfaces

Performed as described in Preparatory example 2, with the exception that the aldehyde functions were introduced in the heparin chain by oxidation with sodium periodate in aqueous solution.

Preparatory Example 6

Attachment of Heparin onto the Inner Lumen of Hollow Fibers

In this preparatory example, a pediatric haemoflow dialyzer was used. The fibers of the dialyzer were made of polysulfone with an inner diameter of 200 microns and a wall thickness of 40 microns. The total surface area of the blood contacting material was 4000 cm$^2$ and the priming volume was 28 ml.

The amination procedure was performed as generally described in Preparatory example 4 with the exception that the etching step was omitted. Polysulfone is hydrophilic and does not need etching. Immobilization of heparin was performed by pumping a solution containing nitrous acid degraded heparin (heparin from Pharmacia) together with NaBH$_3$CN as described in Preparatory example 2. As measurement of the amount of heparin is a destructive procedure, a reference dialyzer that was heparinized under identical conditions was sacrificed and its fibers are subjected to sulfur analysis. The results revealed a heparin content of about 5 μg heparin/cm$^2$, which corresponds to a content of 20 mg heparin in the device.

Preparatory Example 7

Covalent Attachment of Oligomers with Terminal Sialic Acid Residues onto the Inner Lumen of Hollow Fibers In this preparatory example, the aldehyde group at the reducing terminal residue was used for coupling. Amination of the fibers was performed as described in Preparatory example 6 and coupling of the oligosaccharide of formula I, which contains terminal sialic acid residues, was performed by circulating the compound of formula I, dissolved in acetate buffer (800 ml, 0.1 M, pH 4.0) together with NaBH$_3$CN (0.4 g), at room temperature for 24 h. The results revealed a sialic acid content of ca. 2 µg/cm$^2$.

$$
\begin{array}{l}
\text{NeuAc}\alpha\text{2-3Gal}\beta\text{1-4GlcNAc}\beta\text{1} \\
\qquad\qquad\qquad\qquad\qquad\qquad\searrow 6 \\
\text{NeuAc}\alpha\text{2-3Gal}\beta\text{1-4GlcNAc}\beta\text{1-2Man}\alpha\text{1} \\
\qquad | \qquad\qquad\qquad\qquad\qquad\searrow \\
\qquad \alpha\text{1-3Fuc} \qquad\qquad\qquad 6 \\
\qquad\qquad\qquad\qquad\qquad\text{Man}\beta\text{1-4GlcNAc}\beta\text{1-4GlcNAc} \\
\qquad\qquad\qquad\qquad\qquad 3 \\
\text{NeuAc}\alpha\text{2-3Gal}\beta\text{1-4GlcNAc}\beta\text{1-2Man}\alpha\text{1} \\
\qquad\qquad\qquad\qquad\qquad\qquad\nearrow 4 \\
\text{NeuAc}\alpha\text{2-3Gal}\beta\text{1-4GlcNAc}\beta\text{1} \\
\qquad | \\
\qquad \alpha\text{1-3Fuc}
\end{array}
$$

I

Comparative Example 1

Binding of HSV-1 to Heparin in Solution

A solution (10 µl) containing 10$^7$ plaque forming units of virus (Herpes simplex virus type 1 strain KOS321) was incubated with 20 µl of $^3$H-labelled heparan sulfate (HS) in a total volume of 400 µl of buffered NaCl for 30 min at 37° C. Thereafter, the solution was centrifuged through a Microsep 1 M filter, retaining virus and bound HS. 2.3% of HS was bound (479 CPM) to the virus, while 97.7% of the HS was unbound and passed through the filter.

Example 1

Removal of HSV-1 and HSV-2 Virus Particles from Buffered Saline by Binding to Heparin Immobilized on Sephadex Beads Sephadex beads coated with heparin, as in Preparatory example 2, were soaked in buffered NaCl (PBS) and 0.8 ml was transferred to each of two small disposable columns, forming a gel layer of approximately 1 cm. After washing three times, 50 µl of $^3$H-thymidine radiolabelled viruses were suspended in 150 µl of PBS. 10$^9$ plaque forming units of HSV-1, corresponding to 10$^{11}$ virus particles, were added to column 1, and 10$^8$ plaque forming units of HSV-2, corresponding to 10$^{10}$ virus particles, were added to column 2. Virus was allowed to adsorb to the respective columns. Thereafter, 0.8 ml of PBS was added to each column and the pass-through fluid was collected for estimation of unabsorbed virus.

Subsequently, both columns were washed 4 times with 1 ml of PBS, and the washings were collected as fractions for quantification of washed out virus. These, and the following fractions, were transferred to scintillation vials and quantified with regard to amount of virus through determination of cpm in a beta counter. In the next step, the columns were subjected to elution of the respective heparin-bound viruses three times by 1 ml of 2 M NaCl, and the three fractions were collected from each column. Following that, elution was performed by twice adding 1 ml of 5% SDS in PBS (PBS-SDS), and the two fractions from each column were collected. Finally, the heparin-coated beads from the two columns were each suspended in 1 ml of PBS-SDS, and 200 µl aliquots were subjected to quantification of remaining bound virus particles by determination of radioactivity.

The results are shown in Table 1 below. As shown, only 5.5% of HSV-1 particles and 11.7% of HSV-2 particles did not adsorb to the column. Moreover, since the viral DNA and not their heparin-binding proteins are labeled with radioactivity, these non-adsorbed particles might represent non-infectious viruses with disrupted envelopes (i.e. the outer, fragile, parts of the virus that bind to heparin). The rest of the viruses (94.5% for HSV-1 and 88.3% of HSV-2) bind to the heparin-coated beads in the column. The binding appears to be strong, judging from the fact that only 0.5% of HSV-1 and 1.1% of HSV-2 was removed by 4 successive washings. The limited ability of 2 M NaCl at 3 successive attempts to elute the viruses underscores the high-affinity characteristic of the binding of both viruses to the heparin-coated beads. In contrast, substantial quantities of HSV-1 and HSV-2 were eluted by PBS-SDS.

A total of 48% of HSV-1 and 68.8% of HSV-2 were recovered from the columns. This can be attributed to the fact that 2 M NaCl spontaneously decreased the radioactivity of the samples by approximately 30% according to our past observations, and that SDS-PBS probably also has this effect.

Taken together, the results prove the principle that HSV-1 and HSV-2 virus particles can be removed from a fluid phase by passage through a short column containing heparin-coated Sephadex beads, and that extracted viruses bind with high affinity to the columns.

TABLE 1

Binding of radiolabelled HSV virus particles, suspended in buffered NaCl, to heparin-Sephadex beads.
Binding of HSV to heparin column
(% of input virus = control = 100%)

|  | HSV-1 | HSV-2 |
|---|---|---|
| Input virus (control) | 100.0 | 100.0 |
| Unadsorbed virus | 5.5 | 11.7 |
| Washed from column |  |  |
| $1^{st}$ washing | 0.2 | 0.4 |
| $2^{nd}$ washing | 0.1 | 0.3 |
| $3^{rd}$ washing | 0.1 | 0.2 |
| $4^{th}$ washing | 0.1 | 0.2 |
| total unadsorbed + washed | 6.0 | 12.8 |
| Eluted with 2M NaCl |  |  |
| $1^{st}$ elution | 7.8 | 14.7 |
| $2^{nd}$ elution | 1.6 | 1.9 |
| $3^{rd}$ elution | 0.1 | 1.3 |
| Eluted with 5% SDS |  |  |
| $1^{st}$ elution | 10.6 | 11.9 |
| $2^{nd}$ elution | 18.5 | 18.3 |
| total eluted NaCl + SDS | 38.6 | 48.1 |
| Uneluted from beads | 4.1 | 7.9 |
| total uneluted | 4.1 | 7.9 |
| Total recovered (unadsorbed + washed + eluted + uneluted) | 48.7 | 68.8 |

Example 2

Removal of HSV-1 Virus Particles from Human Serum by Binding to Heparin Immobilized on Sephadex Beads The experimental procedure as described in Example 1 was utilized with the difference that the radiolabelled HSV-1 virus particles at a quantity of $10^9$ PFU equivalent to $10^{11}$ virus particles were mixed with 0.5 ml of human serum and then applied on heparin-coated beads in a disposable column. Thereafter, the procedure including elution and washing was followed as in Example 1. The results are shown in Table 2 below.

TABLE 2

Binding of radiolabelled HSV-1 virus particles ($10^{11}$), suspended in human serum, to heparin-Sephadex beads (1 cm³).
Binding of HSV-1 to heparin column
(% of input virus =control = 100%)

| Input virus (control) | 100.0 |
|---|---|
| Unadsorbed virus | 2.4 |
| Washed from column |  |
| $1^{st}$ washing | 0.9 |
| $2^{nd}$ washing | 0.2 |
| $3^{rd}$ washing | 0.1 |
| $4^{th}$ washing | 0.2 |
| total unadsorbed + washed | 3.8 |
| Eluted with 2M NaCl |  |
| $1^{st}$ elution | 2.1 |
| $2^{nd}$ elution | 0.4 |
| $3^{rd}$ elution | 0.2 |
| Eluted with 5% SDS |  |
| $1^{st}$ elution | 3.5 |
| total eluted NaCl + SDS | 6.2 |
| Total recovered (unabsorbed + washed + eluted + uneluted) | 10.0 |
| Remained on beads | 90.0 |

As shown, 97.6% of the HSV-1 particles suspended in human serum were bound to the column. By washing 4 times, only 3.8% of the virus particles were removed. Using 2 M NaCl, only 2.7% of the virus was eluted, and an additional 3.5% were eluted by SDS. The conclusion of these results is that suspending virus in serum, which is the real life situation during severe, disseminated infection, improved the performance of the virus-removing column as regards binding of radiolabelled virus, and that only 2.4% of the HSV-1 particles were unadsorbed. As a probable explanation, serum proteins helped to stabilize the virus particles and thereby improved the removal of HSV-1 by the heparinized Sephadex beads.

Example 3

Removal of HSV-1 Virus Particles from Human Serum by Binding to Heparin Immobilized on a Hollow Fiber Haemoflow Dialyzer The experimental procedure as described in Example 1 was utilized with the difference that the radiolabelled HSV-1 virus particles at a quantity of $10^9$ PFU equivalent to $10^{11}$ virus particles were mixed with 0.5 ml of human serum and then applied on the heparin-coated hollow fiber dialyzer of Preparatory example 6. Thereafter, the procedure including elution and washing was followed as in Example 1. The results are shown in Table 3 below.

As shown, 92.3% of the HSV-1 particles suspended in human serum were bound to the column. By washing 4 times, only 4.2% of the virus particles were removed. By 2 M NaCl, only 4.0% of the virus was eluted, and an additional 4.5% were eluted by SDS. The conclusion of these results is that the binding of virus particles suspended in human serum to heparinized fibers is comparable to that of similarly suspended virus binding to heparin-coated Sephadex beads, and that only 7.7% of the HSV-1 particles were unabsorbed.

TABLE 3

Binding of radiolabelled HSV-1 virus particles, suspended in human serum, to heparinized hollow fibers.
Binding of HSV-1 to heparin column
(% of input virus =control = 100%)

| Input virus (control) | 100.0 |
|---|---|
| Unadsorbed virus | 7.7 |
| Washed from column |  |
| $1^{st}$ washing | 3.1 |
| $2^{nd}$ washing | 0.8 |
| $3^{rd}$ washing | 0.1 |
| $4^{th}$ washing | 0.2 |
| total unadsorbed + washed | 4.2 |

TABLE 3-continued

Binding of radiolabelled HSV-1 virus particles, suspended
in human serum, to heparinized hollow fibers.
Binding of HSV-1 to heparin column
(% of input virus = control = 100%)

| Eluted with 2M NaCl | |
|---|---|
| $1^{st}$ elution | 3.3 |
| $2^{nd}$ elution | 0.5 |
| $3^{rd}$ elution | 0.2 |
| Eluted with 5% SDS | |
| $1^{st}$ elution | 4.5 |
| total eluted NaCl + SDS | 8.5 |
| Total recovered (unabsorbed + washed + eluted + uneluted) | 12.7 |
| Remained on beads | 87.3 |

Example 4

Removal of HSV-1 and HSV-2 Virus Particles from Human Whole Blood by Binding to Heparin Immobilized on Sephadex Beads The experimental procedure as described in Example 1 was utilized with the difference that the radiolabelled HSV-1 and HSV-2 virus particles at a quantity of equivalent to $10^{11}$ virus particles per ml were mixed with 1 ml of human blood and then applied to 1 ml heparin-coated beads in a disposable column. Thereafter, the procedure including elution and washing was followed as in Example 1.

The results are shown in Table 4 below. As shown, 99.1% of the HSV-1 particles and 99.8% of the HSV-2 particles suspended in human blood were bound to the column.

TABLE 4

Binding of radiolabelled HSV virus particles, suspended
in human blood, to heparin-Sephadex beads (1 cm³).
Binding of whole blood HSV to heparin column
(% of input virus = control = 100%)

| | HSV-1 % | HSV-2 % |
|---|---|---|
| Input virus (control) | 100.0 | 100.0 |
| Unadsorbed virus | 0.9 | 0.2 |

Example 5

Removal of Influenza a Virus from Human Serum by Binding to Immobilized Oligosaccharides Containing Sialic Acid Virus stocks of Influenza A H1N1 were replicated in MDCK cells grown at 35° C. under standard conditions for 3 days, after which the cells were homogenized and titrated to assess the number of focus-forming units (FFU)/ml. Virus particles were suspended in human serum to a final concentration of $10^6$ FFU/ml. A 10 ml suspension was applied on a sialic acid-coated hollow fiber dialyzer, prepared using the method described in Preparatory example 7. After titrating the infectivity of the Influenza A-containing serum after passage through the dialyzer and comparing it with titers of an aliquot of the same virus-containing serum not passed through the device it was concluded that 87% of the Influenza A virus FFU remained bound to the fibers.

Example 6

Removal of *Helicobacter pylori* and *Staphylococcus aureus* by Binding to Immobilized Heparin Four sterile pipettes were packed with glass wool (0.5 ml) that was heparinized as described in Preparatory example 3. The "columns" thus formed were washed with 3 ml of sterile phosphate saline buffer (PBS), pH 7.2. Two different strains of *H. pylori* and two different strains of *S. aureus* were tested. Each of the four different bacteria samples, suspended in PBS buffer, were applied to a separate "column". The amounts of bacteria in the samples were measured before application to the column and after elution from the column by optical density (OD) at 560 nm and viable counts (CFU/ml). As is evident from the table below, roughly 90% of *H. pylori* and roughly 50% of *S. aureus* bacteria were immobilized on the columns.

TABLE 6

Binding of *H. pylori* and *S. aureus* to heparinized glass wool.

| Bacteria | $OD_{560}$ In | $OD_{560}$ Out | CFU/ml In | CFU/ml Out | Binding % |
|---|---|---|---|---|---|
| *H. Pylori* ATCC 43504 | 8.33 | 0.81 | $2 \times 10^8$ | $1.5 \times 10^7$ | ~90 |
| *H. Pylori* ATCC 43504 | 8.33 | 1.86 | $2 \times 10^8$ | $1 \times 10^7$ | ~90 |
| *S. aureus* CCUG 12600 | 9.30 | 5.5 | $7.7 \times 10^9$ | $3.6 \times 10^9$ | ~50 |
| *S. aureus* CCUG 12600 | 9.30 | 6.9 | $7.7 \times 10^9$ | $3.6 \times 10^9$ | ~50 |

The invention claimed is:

1. A method for treating a subject in need thereof, by extracorporeal removal of *Staphylococcus aureus*, said method comprising:
   a) contacting said subject's whole blood with heparin immobilized on a solid substrate, said heparin having a terminal residue, wherein heparin immobilization consists of a single covalent link of said terminal residue to said solid substrate by covalent end-point attachment, under conditions allowing binding of said *Staphylococcus aureus* in said subject's whole blood sample to the heparin;
   b) separating the whole blood from the solid substrate;
   c) recovering said whole blood containing a reduced amount of said *Staphylococcus aureus*; and
   d) reintroducing into said subject said whole blood containing a reduced amount of said *Staphylococcus aureus*.

2. The method according to claim 1, wherein said solid substrate comprises microparticles.

3. The method according to claim 1, wherein said solid substrate comprises fibers.

4. The method according to claim 1, wherein the material of said solid substrate is at least one member selected from the group consisting of glass, cellulose, cellulose acetate, chitin, chitosan, crosslinked dextran, crosslinked agarose, polypropylene, polyethylene, polysulfone, polyacrylonitrile, silicone, Teflon and polyurethanes.

5. A method for extracorporeal removal of a pathogenic microbe, wherein said pathogenic microbe is *Staphylococcus aureus*, from human whole blood, said method comprising:
   a) contacting human whole blood with heparin immobilized on a solid substrate by blood flow through a device comprising said solid substrate, said heparin having a terminal residue, wherein heparin immobilization consists of a single covalent link of said terminal residue to said solid substrate by covalent end-point attachment, under conditions allowing binding of said pathogenic microbe, wherein said pathogenic microbe is *Staphylococcus aureus* in said human whole blood sample to the heparin;
   b) separating the whole blood from the solid substrate; and
   c) recovering said whole blood containing a reduced amount of said pathogenic microbe, wherein said pathogenic microbe is *Staphylococcus aureus*.

6. The method according to claim 5, wherein said solid substrate comprises microparticles.

7. The method according to claim 5, wherein said solid substrate comprises fibers.

8. The method according to claim 5, wherein the material of said solid substrate is at least one member selected from the group consisting of glass, cellulose, cellulose acetate, chitin, chitosan, crosslinked dextran, crosslinked agarose, polypropylene, polyethylene, polysulfone, polyacrylonitrile, silicone, Teflon and polyurethanes.

9. The method according to claim 5, wherein said method comprises a continuous loop with the human bloodstream further comprising extracting whole blood from a human before contacting step and reintroducing into said human said blood containing a reduced amount of said pathogenic microbe.

10. The method according to claim 1, wherein said solid substrate comprises a disposable column.

11. The method according to claim 5, wherein said solid substrate comprises a disposable column.

* * * * *